United States Patent [19]

Sistler et al.

[11] Patent Number: 4,975,863

[45] Date of Patent: Dec. 4, 1990

[54] SYSTEM AND PROCESS FOR GRAIN EXAMINATION

[75] Inventors: Frederick E. Sistler; Malcolm E. Wright, both of Baton Rouge, La.

[73] Assignee: Louisiana State University and Agricultural and Mechanical College, Baton Rouge, La.

[21] Appl. No.: 209,092

[22] Filed: Jun. 16, 1988

[51] Int. Cl.⁵ .................. G06F 15/46; B07C 5/00
[52] U.S. Cl. .................... 364/555; 209/643; 358/101; 364/478; 382/8
[58] Field of Search ............ 364/478, 479, 552, 555; 209/702, 643; 382/8, 36; 358/10, 101, 107, 139

[56] References Cited

U.S. PATENT DOCUMENTS

| | | | |
|---|---|---|---|
| 3,348,419 | 10/1967 | Addison | 73/424 |
| 3,478,597 | 11/1969 | Merigold et al. | 73/422 |
| 3,494,217 | 2/1970 | Tanaka et al. | 73/432 |
| 3,555,910 | 1/1971 | Spence et al. | 73/422 |
| 3,595,091 | 7/1971 | Bernutat | 73/432 |
| 4,205,384 | 5/1980 | Merz et al. | 364/555 |
| 4,295,200 | 10/1981 | Johnson | 364/555 |
| 4,344,146 | 8/1982 | Davis, Jr. et al. | 364/552 |
| 4,501,162 | 2/1985 | Mathewes | 73/863.83 |
| 4,514,816 | 4/1985 | Olius et al. | 364/555 |
| 4,543,659 | 9/1985 | Ozaki | 382/8 |
| 4,616,515 | 10/1986 | Dancoine | 73/364.31 |
| 4,707,647 | 11/1987 | Coldren et al. | 364/478 |
| 4,713,781 | 12/1987 | Brizgis et al. | 364/552 |
| 4,759,074 | 7/1988 | Iadipaolo et al. | 382/8 |
| 4,794,647 | 12/1988 | Forgues et al. | 382/8 |
| 4,817,184 | 3/1989 | Thomason et al. | 382/8 |
| 4,818,383 | 4/1989 | Wang | 209/702 |

Primary Examiner—Kevin J. Teska
Attorney, Agent, or Firm—Robert C. Tucker; William D. Kiesel

[57] ABSTRACT

A particle examination system is provided, including a surface which provides a background such that particles on or suspended above the surface are distinguishable from the background; a video camera, for producing an image of the particles against the surface; and an image processor, connected to the video camera, for digitizing the image. A computer is utilized to analyze the digitized data from the image processor, allowing various types of comparisons to be made between the particles examined and a known standard. Additionally, the invention may include a vacuum device which, through holes on the surface, holds the particles in position for examination. A transparent/translucent or transparent surface may be provided, enabling illumination from beneath such plate, allowing analysis of particles for cracks and fissures.

16 Claims, 5 Drawing Sheets

SYSTEM AND PROCESS FOR GRAIN EXAMINATION

BACKGROUND OF THE INVENTION

1. Field of the Invention

This invention relates generally to devices and processes for analysis of particles and, more particularly, to such devices and processes which are used to grade samples of a large collection of particles, such as samples of grain.

1. Prior Art

Particle examination may be accomplished by numerous means. In applications wherein a large number of particles must be sampled and examined it is desirable to examine as many pertinent aspects of each particle as possible given practical time constraints. For the purposes of this application, the word "particle" may encompass any single solid element which forms a part of a group of elements. That is, "particle examination" can include the examination of individual agricultural grains as well as examination of individual ping pong balls in a manufacturing process. Illustrative emphasis shall be placed on agricultural grains.

Present day grain sampling techniques are tedious and time-consuming. A representative sample is taken of a particular grain, such as rice, using any desired sampling technique. The sample is then arranged on a surface such that individual particles may be examined. Normally, the particles are examined by human eye and measured for size, length, breaks, etc. The examiner must record the desired characteristics of each grain in a sample in order to grade the sample accurately. Obviously, this can become a tiring and time-consuming process resulting in estimates of sample characteristics and over-all inaccuracy.

SUMMARY OF THE INVENTION

Therefore, it is an object of this invention to provide a article examination system which allows for examination of each particle of a sample group of particles.

It is another object of this invention to provide such a particle examination system which automatically records the desired characteristics of each particle of a sample group of particles without human examination.

It is still another object of this invention to provide such a particle examination system which automatically separates sample particles for examination and orients the particles for examination.

It is a further object of this invention to provide such a particle examination system which optically measures and then records the desired characteristics of each particle examined.

It is still another object of this invention to provide a particle examination system which allow illumination of particles from beneath the particles in order to examine for cracks and fissures.

Accordingly, a particle examination system is provided, including a surface which provides a background such that particles on or suspended above the surface are distinguishable from the background; a video camera, for producing an image of the particles against the surface; and an image processor, connected to the video camera, for digitizing the image. A computer is utilized to analyze the digitized data from the image processor, allowing various types of comparisons to be made between the particles examined and a known standard. Additionally, the invention may include a vacuum device which, through holes on the surface of the device, holds the particles in position for examination. A transparent/translucent plate may be provided, enabling illumination from beneath such plate, allowing analysis of particles for cracks and fissures.

DETAILED DESCRIPTION OF PREFERRED EMBODIMENTS OF THE INVENTION

Figure 1:
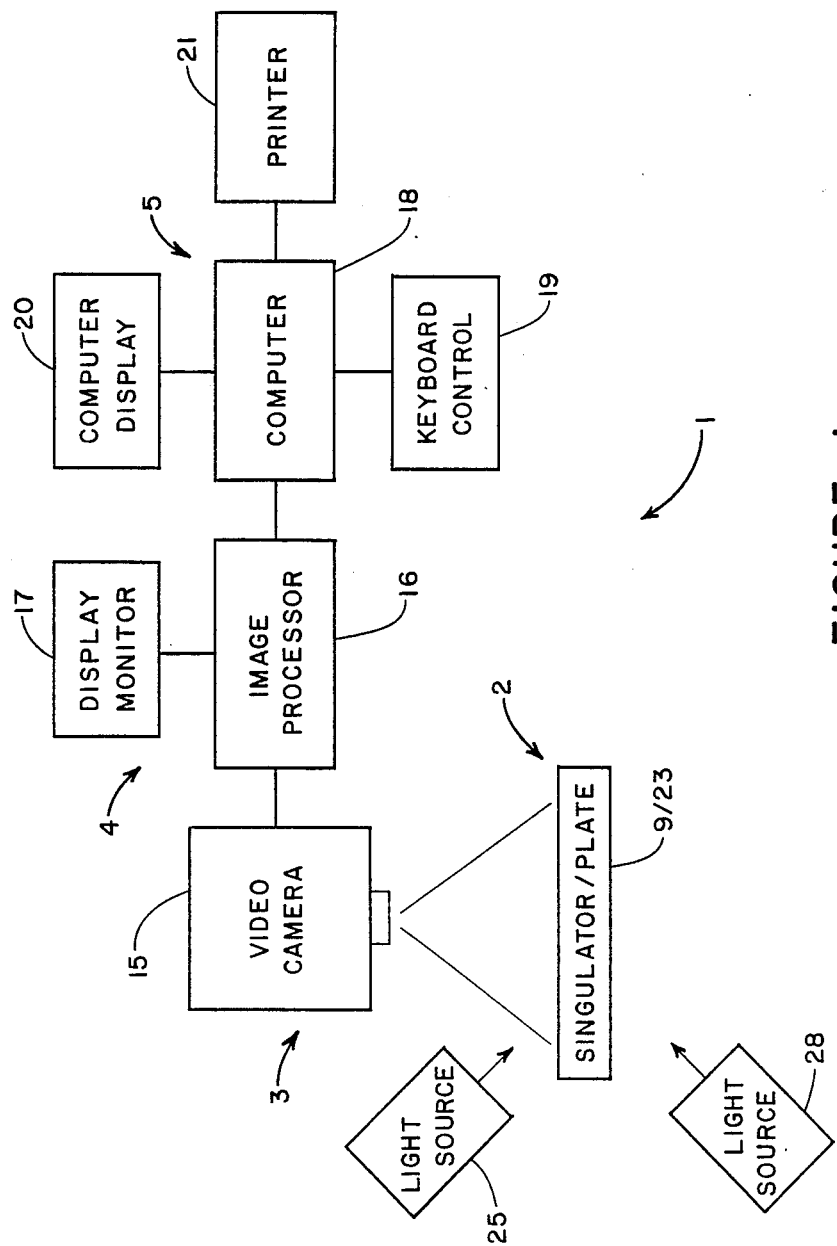
FIG. 1 is a schematic diagram depicting one embodiment of the particle examination system of this invention.

As shown schematically in FIG. 1, the particle examination system 1 includes a means 2, for arranging particles for viewing, a video means 3, for producing an image of the particles, and an image processing means 4, for digitizing the image. Ideally, the data from image processing means 4 must be analyzed and the entire system 1 controlled. Therefore, a computing means 5 is utilized to perform these functions. The system 1 allows the user to analyze particle samples quickly and accurately without tedious hand measurement of particle sizes. The ensuing detailed descriptions of components and process steps will emphasize application of the system 1 to the analysis of samples of grain. The embodiments shown in the Figures are particularly suited for the analysis samples of rice.

Figure 2:
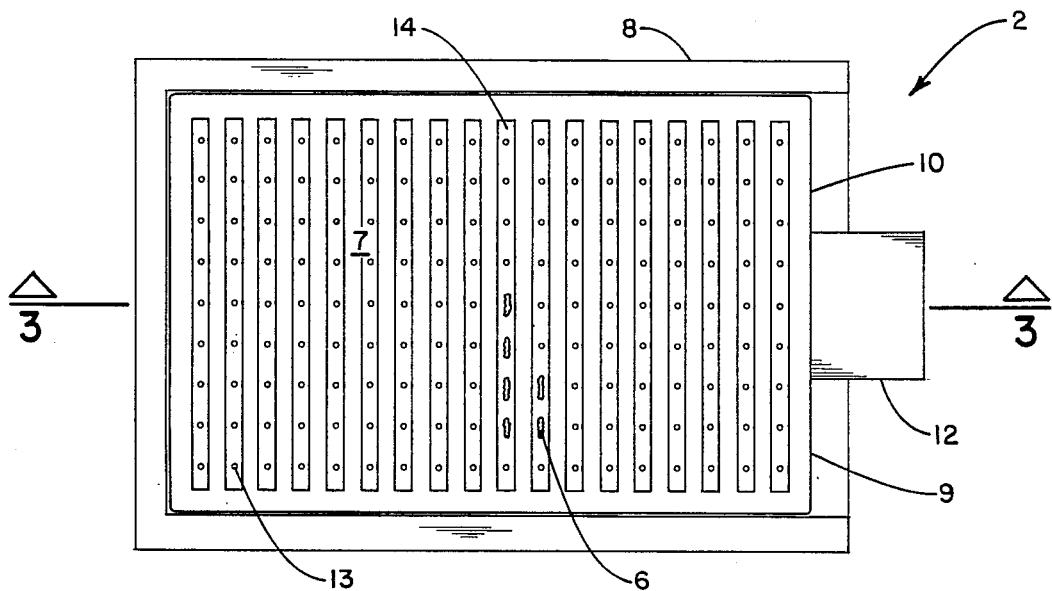
FIG. 2 is a top view of the singulator of this invention.
Figure 3:
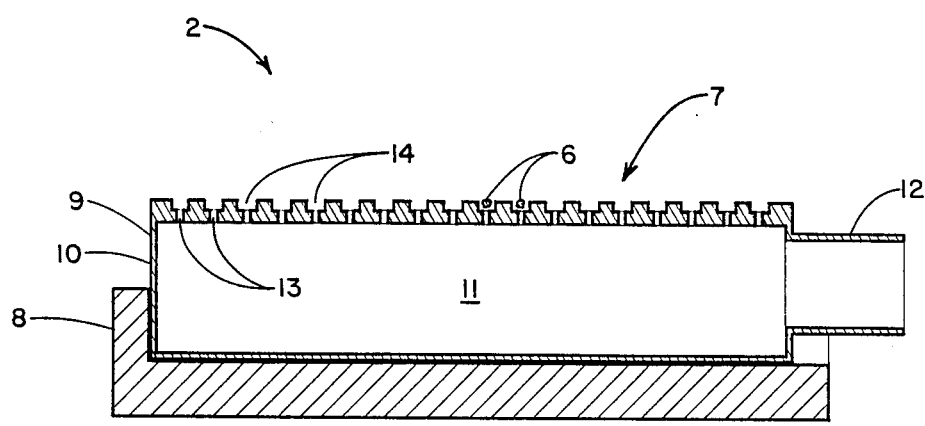
FIG. 3 is a sectional view of the singulator of this invention taken along line 3—3 of FIG. 2.

In order to perform any meaningful examination of particle for size, cracks, fissures, etc. the particles should be arranged such that each particle may be individually examined. Ideally, the particles 6 (shown in the Figures as rice grains) should not touch each other. Therefore, the means 2, for arranging particles 6 for viewing, should accomplish these objectives. As shown in FIGS. 2 and 3, such means 2 may comprise a surface 7 on which particles 6 may be arranged. The surface 7 should be configured to accept the particular particles 6 being examined so as to allow orderly scanning of the particles 6 by video means 3. In order for the surface 7 to be accurately positioned with respect to video means 3, a fixture 8 is provided. Thus, surface 7 will be oriented properly each time it is placed in the field of view of video means 3.

While automatic alignment of particles 6 is not required, it is certainly preferred that means 2 automatically separate and align, or singulate, the particles on surface 7. Singulator 9, shown in FIGS. 2 and 3, accomplishes this purpose. Singulator 9 comprises a hollow body 10 having an interior cavity 11. Interior cavity 11 is connectable to any conventional vacuum source (such as a vacuum pump), not shown, via vacuum connection 12. Surface 7 forms the top of body 10, and is provided with at least one hole 13 communicating with interior cavity 11. Thus, when vacuum is applied to interior cavity 11 and particles 6 are poured over surface 7, or surface 7 is placed in a sample of particles 6, particles 6 are drawn to and held in place over holes 13. Of course, holes 13 must be smaller than the particles 6 being examined, but large enough to apply enough suction to hold particles 6 in place. Holes 13 are aligned for even distribution of particles 6 over surface 7, and are spaced such that individual particles 6 will not touch each other. Additional alignment is provided by grooves 14 which orient rice particles 6 in the same direction for accurate scanning by video means 3. Of course, when particles 6 other than rice are examined, an alternate orientation means may be utilized depending upon the shape of the particle. For example, for round-shaped particles 6 it may be desirable to provide indentations, or dimples, around each hole 13 in order to more easily guide particles 6 to each hole 13.

Surface 7 should provide a background which is of sufficient color differential from particles 6 that video means 3 is able to easily distinguish the contrast between particles 6 and surface 7, when particles 6 are illuminated by a light source 25, 28. For rice, which is primarily a white color, surface 7 should be black or a very dark color.

Video means 3 preferably comprises a video camera 15, which is focused on surface 7. A typical video camera 15 which may be used with the system 1 is a Pulnix TM34 CCD camera. Camera 15 typically scans either in verticle or horizontal lines, usually horizontal. Therefore, it is preferable that surface 7 be positioned such that particles 6 are aligned either perpendicular or parallel to the scanning pattern of camera 15. The pattern of holes 13 on surface 7 is therefore preferred to align particles 6 in the desired scanning pattern. Of course, grooves 14 aid significantly in the alignment of elongated particles 6, such as rice grains. The video output of video means 3 is connected to image processing means 4.

Image processing means 4 digitizes the image produced by video means 3. Once in digital form, the image can be processed by computing means 5, which may comprise any conventional computer. Image processing means 4 preferably takes the form of a conventional image processor 16, such as an Imaging Technologies, Inc. Series 151 image processor. Once in digital form, the image consisting of the contrasted particles 6 against surface 7 can be analyzed to evaluate desired parameters relating to particles 6. A display monitor 17, such as a 12-inch Sony RGB monitor, may be connected to image processor 16 to view the digitized image produced by image processor 16.

The Imaging Technologies Series 151 image processor contains the following boards:
ADI-150—Analog to digital interface—Digitizes the image coming from the video camera into a 512 by 512 pixel image, with 256 grey levels per pixel—Displays the image on a video monitor. FB-150—Frame buffer Stores digitized images and outputs them to other modules in the processing system—Contains memory for storing three images simultaneously.
ALU-150—Pipeline processor—This is a computation module used in conjunction with the ADI-150 and the FB-150. It is used to perform image averaging, subtraction, convolutions, thresholding, as well as other operations not related to this application.
Interface—An interface board plugs into the computer to serve as the interface between the image processing system and the computer.

Computing means 5 preferably comprises an IBM PC/AT (or equivalent) microcomputer system 18 having keyboard control 19, display 20 and printer 21. Program control for computer 18 is provided in accordance with the desired analysis of the particles being examined. It is, or course, desirable to have computer 18 control and thus automate as much of the sampling process as possible.

An appendix, available in the application file, contains six suggested programs for operation of the system to examine rice kernels. Each of the following computer program modules performs multiple tasks. A description of those tasks is also provided below. It should be noted that these programs are specific to the Imaging Technologies hardware used. The algorithms are applicable to other video digitizing systems, but the programs would have to be adapted to the specific resolution, control commands and software subroutines supplied with the hardware, as well as number of grey levels associated with the selected hardware.

GENERAL.C

This file contains functions for initializing the boards in the image processing system and averaging images.
1. Initialize the system, select the necessary processing boards, and initialize the appropriate registers on the boards.
2. Average 8 consecutive images and store the resultant image.

HISTO.C

1. Scale grey level values for histogram.
2. Write histogram of image grey levels into a memory buffer.
3. Draw histogram onto video monitor.
4. Replace a video image with a binary image consisting of two grey (brightness) levels—a low number grey level represents all grey levels equal to or below a selected grey level, and a high number grey level represents all grey levels above the selected gray level.

CALIB.C

Routines are provided for calibrating the system when it is first used or whenever any changes in equipment, lighting, or camera focal length are made.
1. Find a threshold and calibrate for length and weight per pixel. The threshold must be a grey value such that the length and weight of the kernels show the least change when the threshold is changed.
2. Allow the user to install the camera at the correct distance to the objects. After installation, a length of approximately 5 pixels in the image along the vertical axis will correspond to a real length of 1.0 mm (0.0393 inch).

RICELAY.C

This program module displays results of rice grading system on the monitor.
1. Initialize the image processor video output.
2. Create and display pie charts of whole, cracked, and broken kernels by number and by weight.
3. Calculate and display on the monitor the numerical results of the grading.
4. Calculate and display bar graphs of the grading results.

5. Create a disk file on the computer which contains the grading results.

AOI.C

This program allows the user to define a rectangular area of interest in a digitized image for further processing and/or analysis. The area of interest can be smaller than the total image. The area of interest can be specified using the arrow keys on the computer's keyboard. A set of crosshairs are superimposed on the image and used to define the opposite corners of the rectangular area of interest.

KERNELS.C

This program contains functions dealing specifically with kernels (particles 6) in the images.
1. Find kernels in a thresholded image. Check sizes of kernels to see if they are valid kernels. Create error message if kernels are too large (such as two kernels touching each other) and allow user to correct problem.
2. Examine known kernels in image for cracks and brokens. Brokens are defined as kernels less than two-thirds the length of a preset length defined for a particular variety.
3. Find cracked kernels. Define rectangular area just small enough to be contained within the kernel and average and variance of pixel values for horizontal rows within the rectangle. Perform Fast Fourier Transform on horizontal rows. Calculate power spectrum. Examine coefficients for spectrum values 10 to 19. Square the real and imaginary coefficients for each of these terms, add them together, take the square root, then take the logarithm of the square root. Average three groups of these logarithms for spectrum values 10 to 14, 13 to 18, and 15 to 19. If two of the three average values are greater than a preset level, define the kernel to be cracked. Otherwise, it is defined as not cracked.

GRADE.C

This is the main program for the grading system. It performs the following operations.
1. Calibrate the system. Specify pixel length per millimeter, grey value threshold, and thresholds for the Fourier power spectrum values.
2. Get the image of a subsample of rice. A sample of rice may consist of several subsamples. Get the image and check whether or not it is a valid image. An invalid image contains images too small or too large to be single kernels. If a valid image, locate kernels and measure dimensions of all kernels.
3. Find which kernels are broken. Broken kernels are not checked for cracks.
4. Find cracked kernels.
5. Store the data related to the processed image, including: total number of kernels, number of broken kernels, number of cracked kernels, total weight of kernels, weight of broken kernels, weight of cracked kernels, and length of kernels, separated into ten length classes.
6. Ask user if there are more subsamples. If yes, go to step 2 and repeat the process. If no, proceed to step 7.
7. Present results of sample on monitor, printer (optional), and store on disk file.

Figure 4:
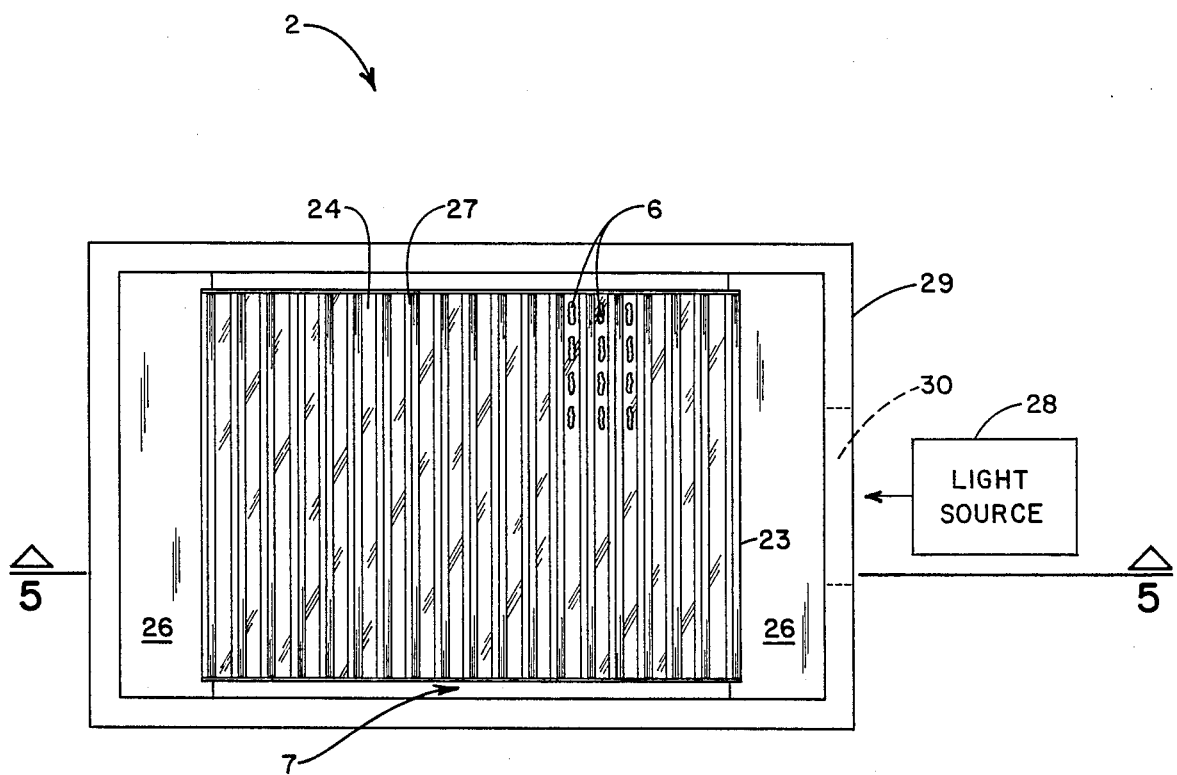
FIG. 4 is a top view of the crack detection plate of this invention.
Figure 5:
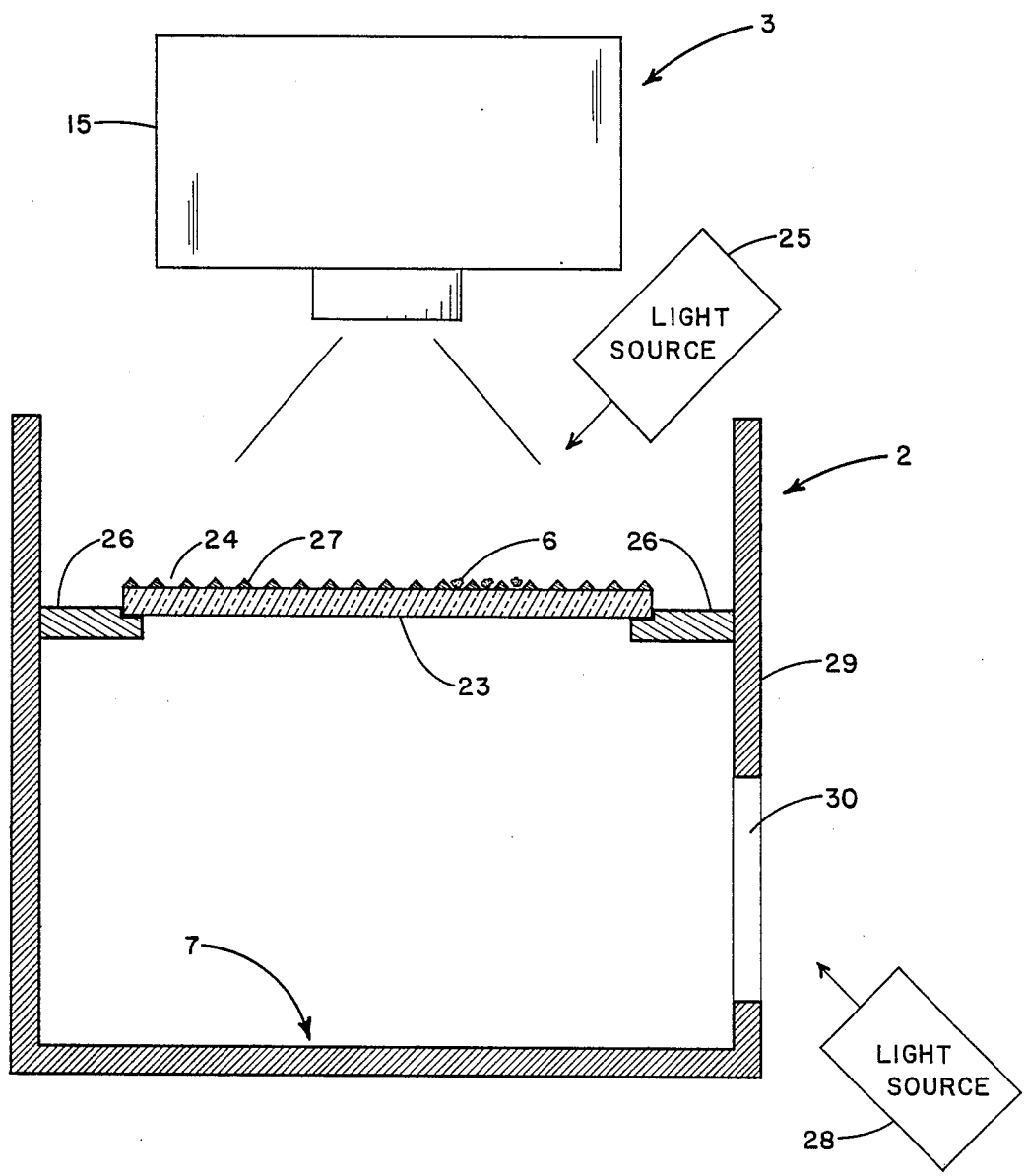
FIG. 5 is a sectional view of the crack detection plate of this invention taken along line 5—5 of FIG. 4.

It is desirable to analyze particles 6 to determine the presence of cracks or fissures. In order to do so, it is necessary to illuminate the particles 6 from beneath means 2 for arranging particles for viewing. In its most simple form, such a means 2 comprises a transparent or translucent plate 23 of clear material such as plexiglass or glass on which particles 6 may be arranged for illumination from beneath plate 23. For purposes herein, the term "transparent" shall encompass "translucent". A transparent plate is preferred. However, a translucent surface will suffice if light is sufficiently transmitted through plate 23 without illuminating plate 23. Illumination should be at an oblique angle to plate 23. A surface 7 provides a dark background behind grain particles 6. By illuminating particles 6 at an oblique angle, particles 6 glow against background 7, with cracks and fissures appearing dark to camera 5, enabling detection and recordation by the system 1. As shown in FIGS. 4 and 5, it is preferred that plate 23 be provided with grooves 24, which are alignable with grooves 14 of singulator 9. Thus, once particles 6 are collected and/or analyzed on singulator 9 they can easily be transferred to plate 23 while maintaining a vacuum on singulator 9 to hold particles 6 in place in grooves 14, inverting singulator 9 and aligning grooves 14 with grooves 24 on plate 23 and releasing the vacuum on singulator 9. Particles 6 will then fall into grooves 24 on plate 23 thus spacing particles 6 just as they were on singulator 9. Grooves 24 are preferably created by the addition of darkened strips 27 to plate 23. Strips 27 aid in the illumination of particles 6 from beneath plate 23 against a dark background surface 7. A fixture 26 holds plate 23 in place.

Figure 6:
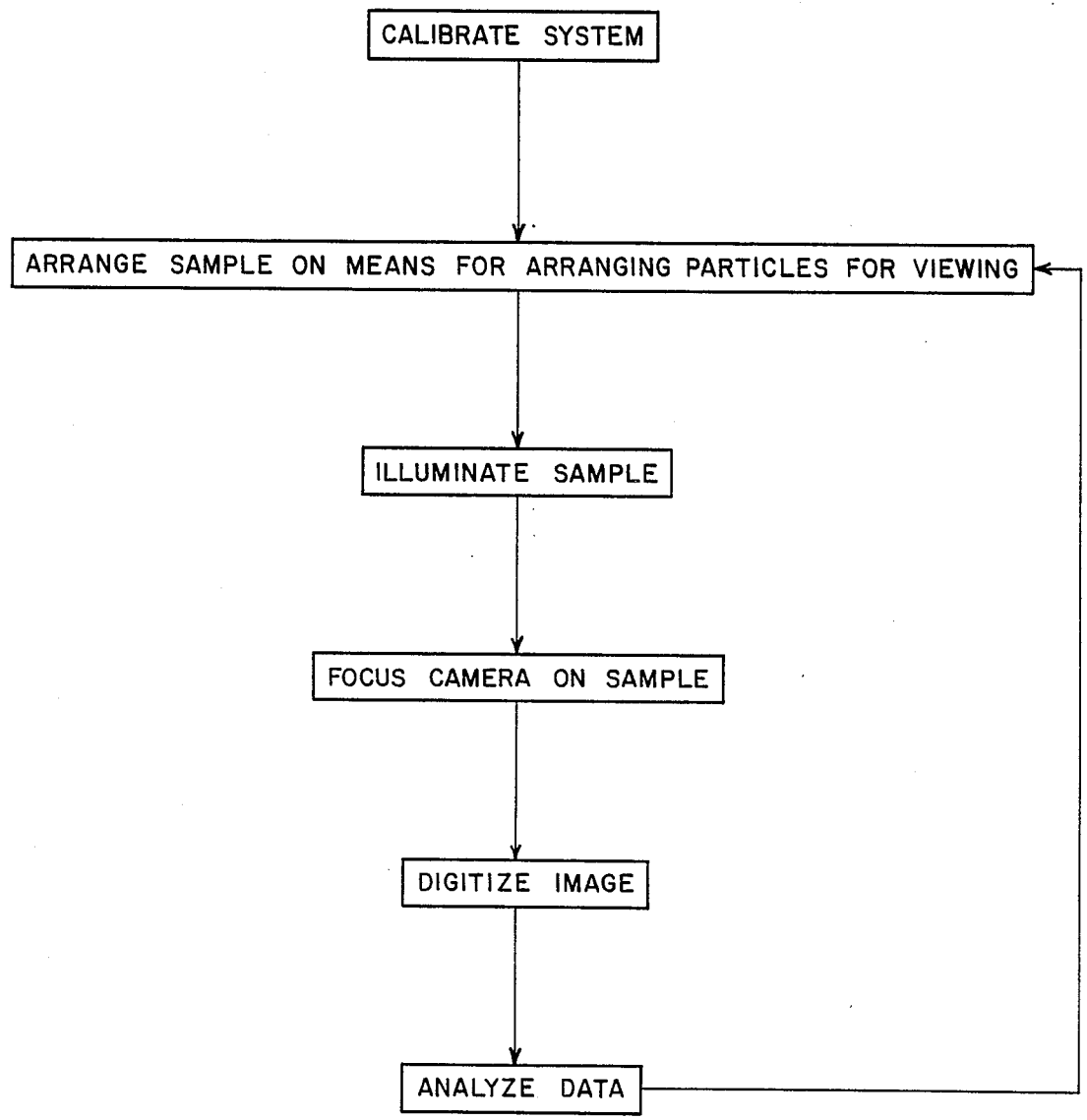
FIG. 6 is a flow chart showing an embodiment of the process of the invention.

FIG. 6 generally depicts the steps involved in particle examination. The system 1 is calibrated for length and width measurements by placing a disk of known diameter on fixture 8, 26 in the field of view of video camera 15. The camera lens is focused on the disk. The diameter of the disk is entered into computer 18. A video image of the disk is transmitted from camera 15 to image processor 16 and computer 18 where the image is digitized and analyzed. The digitized image is used with the diameter of the disk for the system 1 to calibrate itself.

Once the system 1 is calibrated it is ready for particle analysis. A vacuum is applied to singulator 9 through vacuum connection 12. The singulator 9 is place within a sample of grain or other particles 6, or the sample can be poured over singulator 9. Particles (grains) 6 are automatically aligned in grooves 14 and are held on surface 7 by the vacuum through holes 13. The singulator 9 is then placed in fixture 8 with surface 7 facing up toward camera 15. The vacuum may be removed once singulator 9 is in fixture 8. Overhead lighting 25 is used to illuminate surface 7 while size measurements are made.

The video image of surface 7 and grains 6 is digitized and thresholded to form a binary (two gray level) image consisting only of grain (particle) elements (pixels) and background. The image may then be analyzed as desired to record the sizes of grains 6 utilizing the programs listed in the Appendix. The length and silhouette area of each grain 6 are measured and recorded. The length of each grain 6 is compared with the defined standard length for the variety of grain. The silhouette area of each grain is correlated to its weight through the use of a formula relating the grain weight to its area.

After size measurements are complete, the vacuum is reapplied and the singulator 9 is inverted and placed on plate 23, aligning grooves 14 with grooves 24. The vacuum is released and the grains 6 are then deposited on plate 23. The overhead lighting 25 is extinguished and the sample is illuminated from beneath plate 23 by light source 28 at an oblique angle. An image of the sample and plate 23 is then acquired by camera 15 and analyzed for cracks within the sample again utilizing the programs in the appendix, available in the application file, or other desired analysis technique.

The entire examination process could be accomplished utilizing plate 23, as shown in FIGS. 4 and 5. Once the particles 6 are deposited on plate 23 (by singulator 9 or by any other means), a dark background surface 7 is placed under and preferably around plate 23 for illumination from above by overhead lighting 25. The overhead lighting 25 can then be extinguished and plate 23 may be illuminated from below by light source 28 for crack detection. Thus, means 2, for arranging particles for viewing, may comprise a separate apparatus from surface 7, which may only be utilized to provide background contrast. One such possible embodiment calls for support of particles 6 on a grid formed by strips, wires, plate 23 or other support media suspended in a dark box 29, as shown in FIGS. 4 and 5. Illumination from above will result in contrast against the darkened background surfaces 7 of the box 29. Illumination through opening 30 within the box will result in background illumination of the grains 6 for crack detection.

The system 1 must be re-calibrated when there is a change in any of the following parameters:
1. Distance from camera 15 to grains 6;
2. Grey value threshold—i.e. grey level (light intensity) of image which differentiates between a grain 6 and the background surrounding the grain 6;
3. Pixel length/mm—a picture element (pixel) has a given length in millimeters; the resolution must be approximately 5 pixels per millimeter in the vertical direction;
4. Weight, pixel/mg—the equivalent weight of grain encompassed by an area of one pixel; or
5. Thresholds for Fourier power spectrum values—the light intensity value used in the Fourier power spectrum.

Analysis for broken grains 6 or fissure detection continues by acquiring the image of a subsample. This is accomplished by the "get_sub_sample" function in the programs in the Appendix. This function acquires a digital image of the sample, checks to see if there are any grains 6 within the image, locates all kernels (grains 6) using the function "find_kernels", and measures the dimensions of all kernels 6 in number of pixels per kernel 6.

It is desirable to determine which kernels 6 are broken. Kernels 6 are defined as broken if they are less than a given percentage of a full kernel length. For rice, a broken kernel 6 may be defined as less than two-thirds the length of a whole kernel 6 of a short, medium, or long grain, depending on the variety. The percentage varies with the grain and the variety of grain. Broken kernels 6 are not examined for cracks.

Cracks are found using the function "find_cracks", only examining non-broken kernels 6. A rectangle is defined within each kernel 6 ten pixels from the top and bottom of the kernel 6 and three pixels in from each side. The average grey level is calculated across each horizontal line of pixels within the defined rectangle. A Fourier analysis is performed on the average for each row (horizontal line) of pixels. The values of the Fourier analysis are used to determine whether or not the kernel is cracked. The Fourier analysis uses a Fast Fourier Transform of the average of each horizontal line of pixels within the rectangle. The power spectrum is calculated. The coefficients for spectrum values 10 to 19 are used. The real and imaginary coefficients for each of these terms are squared and added together, the square root is taken, and finally the logarithm of the square root is calculated. The average of three groups of these logarithms for spectrum values 10 to 14, 13 to 18, and 15 to 19 are calculated. If two of the three average values are greater than a preset level, the kernel 6 is defined as "cracked". Otherwise, it is defined as "not cracked".

The type of data which is desirable to be stored on a disk file is as follows: total number of kernels, number of broken kernels, number of cracked kernels, total weight of kernels, weight of broken kernels, weight of cracked kernels and length of kernels (classified into ten groups).

Multiple samples are generally allowed to be considered as one large sample, up to a total of 10,000 grains 6 per sample. The total number of grains 6 and the percent broken both by number and by weight are displayed in tabular and graphical (pie-chart) form on the monitor 20. An option is provided for also printing the results on printer 21.

Of course, the entire system 1 and process may be automated for high volume sampling. The elements of this invention may be varied by those skilled in the art to achieve desired examination results, and such alternate embodiments are intended to be included within the scope and spirit of the following claims.

I claim:
1. A grain examination system, comprising:
   a. a means for supporting, separating and arranging a plurality of grain kernels for viewing, including:
      i. a background surface of such color that said kernels are distinguishable from said background surface;
   b. a light source for illuminating said kernels in contrast to said background surface;
   c. a video means, for producing an image of said kernels in contrast to said background surface;
   d. an image processing means for digitizing said image, connected to said video means; and
   e. a computing means for identifying desired characteristics of each said kernel and comparing said characteristics to a desired standard, connected to said image processing means.
2. A grain examination system according to claim 1, wherein said means for supporting, separating and arranging grain kernels for viewing further includes:
   ii. a transparent plate for allowing illumination from beneath said grain kernels, positioned above said background surface.
3. A grain examination system according to claim 1, wherein said means for supporting, separating and arranging grain kernels for viewing further includes:
   ii. a singulator, having a hollow body including an interior connectable to a vacuum source, said body having a surface forming one side of said body, said surface having a plurality of holes therein opening between said interior and said surface, each of said holes being smaller than said kernels, said holes being spaced apart such that kernels covering adjacent said holes will not touch each other.
4. A grain examination system according to claim 3, wherein said surface of said hollow body includes said background surface.

5. A grain examination system according to claim 3, wherein said means for supporting, separating and arranging grain kernels for viewing further includes:
   iii. a transparent plate for supporting said grain kernels and allowing illumination from beneath said grain kernels, positioned above said background surface.

6. A grain examination system according to claim 3, wherein said transparent plate is provided with at least one groove.

7. A grain examination system according to claim 6, wherein said groove of said transparent plate is formed by a pair of opaque strips attached to said plate.

8. A grain examination system according to claim 3, wherein said surface of said hollow body is provided with at least one groove for aligning said grain kernels and at least one said hole is provided within said groove.

9. A grain examination system according to claim 8, wherein said means for supporting, separating and arranging grain kernels for viewing further includes:
   iii. a transparent plate for supporting said grain kernels and allowing illumination from beneath said grain kernels, positioned above said background surface.

10. A grain examination system according to claim 4, wherein said transparent plate is provided with at least one groove, alignable with said groove of said surface of said hollow body.

11. A grain examination system according to claim 10, wherein said groove of said transparent plate is formed by a pair of opaque strips attached to said plate.

12. A singulator for supporting, separating and arranging grain kernels for viewing, comprising a hollow body including an interior connectable to a vacuum source, said body having a surface forming one side of said body, said surface having a plurality of holes therein opening between said interior and said surface, each of said holes being smaller than said kernels, said holes being spaced apart such that kernels covering adjacent said holes will not touch each other.

13. A singulator for supporting, separating and arranging grain kernels for viewing according to claim 12, wherein said surface of said hollow body is provided with at least one groove and at least one said hole is provided within said groove.

14. A method for grading samples of grain containing a plurality of grain kernels, comprising the steps of:
   a. arranging a plurality of kernels, such that said kernels do not touch each other, on a means for supporting, separating said arranging said kernels for viewing, which includes a background surface of such color that said kernels are distinguishable from said background surface;
   b. illuminating said kernels;
   c. focusing a video means, for producing an image of said kernels in contrast to said background surface, on said kernels and producing an image of said kernels;
   d. digitizing said image and processing said image to form data reflecting characteristics of said image; and
   e. analyzing said data.

15. A method for grading samples of rice containing a plurality of rice kernels, comprising the steps of:
   a. arranging a plurality of rice kernels, such that said kernels do not touch each other, on a means for supporting, separating and arranging said kernels for viewing, which includes a background surface of such color that said kernels are distinguishable from said background surface;
   b. illuminating said kernels;
   c. focusing a video means, for producing an image of said kernels in contrast to said background surface, on said kernels and producing an image of said kernels;
   d. digitizing said image and processing said image to form data reflecting characteristics of said image; and
   e. analyzing said data for each said kernel.

16. A method for grading samples of rice containing a plurality of rice kernels according to claim 15, wherein said step of analyzing said data includes calculating the size of said kernels, which said kernels are broken and which said kernels are cracked.

* * * * *

UNITED STATES PATENT AND TRADEMARK OFFICE
CERTIFICATE OF CORRECTION

PATENT NO.  : 4,975,863

DATED       : December 4, 1990

INVENTOR(S) : Frederick E. Sistler and Malcolm E. Wright

It is certified that error appears in the above-identified patent and that said Letters Patent is hereby corrected as shown below:

In Column 1, Line 40, "a article examination" should read --a particle examination--.

In Column 6, Line 16, "and recordation" should read --and recording--.

In Column 6, Line 44, "is place within" should read --is placed within--.

In Column 7, Line 1, "is extinquished" should read --is extinguished--.

Signed and Sealed this

Twenty-third Day of June, 1992

Attest:

DOUGLAS B. COMER

Attesting Officer

Acting Commissioner of Patents and Trademarks